United States Patent [19]

Jolles et al.

[11] 3,956,481

[45] May 11, 1976

[54] HYDROSOLUBLE EXTRACTS OF MYCOBACTERIA, THEIR PREPARATION AND USE

[75] Inventors: Pierre Jolles, Paris; Daniele Migliore-Samour, Kremlin-Bicetre, both of France

[73] Assignee: Agence Nationale de Valorisation de la Recherche (ANVAR), Neuilly-sur-Seine, France

[22] Filed: June 19, 1973

[21] Appl. No.: 371,658

[30] Foreign Application Priority Data
June 20, 1972 France .............................. 72.22208
May 4, 1973 France .............................. 73.16130

[52] U.S. Cl. ................................................. 424/92
[51] Int. Cl.² ........................................ A61K 39/02
[58] Field of Search ........................................ 424/92

[56] References Cited
UNITED STATES PATENTS
3,529,057   9/1970   Tsuchiya et al. ........................ 424/92

OTHER PUBLICATIONS
Engibarov—Chem. Abst., Vol. 68 (1968), p. 85115t.
Birnbaum et al.—Chem. Abst., Vol. 71 (1969), 109957j.
Motomiya et al.—Chem. Abst., Vol. 70 (1969), p. 65420b.
Roszman et al.—Chem. Abst., Vol. 68 (1968), p. 76570k.
Goeing et al.—Chem. Abst., Vol. 66 (1967), p. 74398v.
Adam et al., Chemical Abstracts 77: 17903j (1972).
Chedid et al., Chemical Abstracts 77: 17904k (1972).

Primary Examiner—Norman A. Drezin
Attorney, Agent, or Firm—Burgess, Dinklage & Sprung

[57] ABSTRACT

Hydrosoluble extracts of mycobacteria suitable as immunological adjuvants are prepared. These extracts have a molecular weight between 3,500 and 30,000 and adjuvant, non-arthrogen properties. The delipidated bacterial residues of mycobacteria are subjected to a mild extraction, then the so-obtained substance is isolated and purified by physicochemical methods, or the delipidated bacterial residues of mycobacteria are treated by means of pyridine, optionally in the presence of acetic anhydride, then the obtained products are treated with ethanol or water, and the hydrosoluble substances are isolated and purified by physicochemical methods.

6 Claims, No Drawings

HYDROSOLUBLE EXTRACTS OF MYCOBACTERIA, THEIR PREPARATION AND USE

The present invention relates to hydrosoluble extracts of mycobacteria, their preparation and use as immunological adjuvants.

Certain mycobacterial preparation have the property of stimulating antibody formation [J. Freund, Adv. Tuberc. Res., 7, 130 (1956)] but have certain drawbacks such as the induction of experimental arthritis in the rat [B. H. Waksmann and coll., Immunology, 1, 54 (1968); R. G. White and coll., Immunology 7, 158 (1964)]. In these different active substances a polysaccharide (Poly) is linked to a peptidoglycane (PA).

More particularly, a "D wax" of Mycobacterium tuberculosis var-Hominis consists of a lipid portion linked by ester bonds to a hydrosoluble Poly-PA portion.

It is possible to obtain the hydrosoluble (Poly-PA) portion by chemical methods such as saponification [J. Asselineau, C.R. Acad. Sci., 229, 791 (1949)] or acetylation [P. Jollès and coll., Immunology, 14, 159 (1968)] or by biochemical methods which bring on the action of an enzyme [Adam A. and coll, Proc. Nat. Acad. Sci. USA 69, 851 (1972); Yanagida, Chem. Abstr., 76, 137 850 r (1972)]. All these hydrosoluble portions obtained by chemical or biochemical methods are not regularly active as immunological adjuvants. This irregular behaviour is notably due to more or less substantial modifications caused to sugars.

It has now been found, and it is this which is the object of the present invention, that starting with mycobacteria delipidated by treatments which do not destroy the sugars or which do not necessitate the use of enzymes, hydrosoluble products can be obtained which have an adjuvant and non-arthrogen activity.

The hydrosoluble extracts according to the present invention are substances, the molecular weight of which may be comprised between 3,500 and 30,000. In all these substances a nitrogenous portion, the structure of which may be compared with the structure of the peptidoglycane of the wall, is associated with reducing non-aminated sugars such as mannose, glucose, galactose, arabinose.

These substances may be obtained from delipidated bacterial residues of mycobacteria according to the method of A. Aebi and coll. Bull. Soc. Chim. Biol: 35, 661 (1953).

either by mild extraction (homogenization in aqueous medium) followed by the application usually used of physico-chemical methods of isolation and purification, such as salting out, centrifugations, dialysis and chromatographies, or by action of the pyridine optionally in the presence, of acetic anhydride, followed by ethanol or water extractions and the application of the usually used methods of isolaton and purification such as salting out, centrifugations, dialysis and chromatographies.

Thus the mild extraction provies a hydrosoluble extract which is called "Poly-PA" and which has the following characteristics:

appearance: pulverulent white powder (after freeze-drying)
composition:
- a. amino acids (molecular ratio): alamine (3), glutamic acid (2), $\alpha,\alpha'$-diaminopimelic acid (2)
- b. amino sugars (molecular ratio): N-acetylglucosamine (2), N-glycolylmuramic acid (2); and presence of N-acetylgalactosamine
- c. non-amino reducing sugars: arabinose, galactose; and presence of mannose
- d. lipids: less than 0.5% molecular weight (calculated on the basis of three alanine residues per molecule) $14,000 \pm 2,000$
sedimentation constant $S_{20}$ (detetminated with a Beckman apparatus): 2

The treatment with pyridine in the presence of acetic anhydride provides a hydrosoluble substance designated as "Substance A" and having the following characteristics:

appearance: pulverulent yellow powder (after freeze-drying)
composition:
- a. aminoacids (molecular ratio): alanine (3) glutamic acid (2), $\alpha\text{-}\alpha'$-diaminopimelic acid (2)
- b. amino sugars (molecular ratio): N-acetylglucosamine (2), N-acetylmuramic acid (2)
- c. non-amino reducing sugars: mannose, glucose, presence of arabinose; absence of galactose
- d. absence of lipids molecular weight (calculated on the basis of three alanine residues per molecule) $4,000 \pm 200$
Sedimentation constant $S_{20}$ (determined with a Beckman apparatus): 0.7

The treatment with pyridine alone provides two hydrosoluble substances: the one having a high molecular weight ($26,500 \pm 500$) which is called "Substance B", the other of low molecular weight which is herein called "Substance C".

Substance C has the following characteristics:
appearance: white powder after freeze-drying
composition:
- a. amino acids (molecular ratio): alanine (3), glutamic acid (2), $\alpha,\alpha'$-diaminopimelic acid (2)
- b. amino sugars (molecular ratio): N-acetylglucosamine (2), N-glycolylmuramic acid (2)
- c. non-amino reducing sugars: arabinose galactose, mannose.

molecular weight (calculated on the basis of three alanine residues per molecule) $6,000 \pm 500$.

The mycobacteria which may be used for carrying out the process according to the invention are the virulent or non-virulent mycobacteria of human or nonhuman origin, in which the existence of a "D wax" has been indicated. Among the mycobacteria which may be used there may be mentioned: *Mycobacterium tuberculosis*, var. *hominis*, *Mycobacterium kansasii*, *Mycobacterium tuberculosis*, var. *bovis*, strains LA and BB, etc. . . .

The hydrosoluble substances obtained according to the present invention have an adjuvant and non-anthrogen activity.

The adjuvant power is determined in the Hartley strain guinea pig according to the principle of the method of R. G. White and coll., Immunology, 7, 158 (1964) and the anthrogen and protective powers according to the methods described by F. Bonhomme, C.R. Acad. Sci., Series D, 263, 1, 422 (1966) and C.R. Acad. Sci., Series D, 265, 211 (1967)

In the guinea pig, the hydrosoluble substances according to the invention provide an increase of the antibodies level at doses higher than, or equal to, 0.1 mg by introdermic injection.

The new products according to the invention can be used in human or veterinary medicine to enhance the resistance to infections of viral or bacterial origin. They provide an increase of the antibodies formation useful to control pathogenic organisms and they may be associated with the administration of vaccines to ensure the maximum reaction of antibodies.

The present invention also relates to pharmaceutic compositions containing at least one hydrosoluble substance according to the invention associated with one or more compatible diluents or adjuvants and optionally with other medicaments such as antibiotics, lipids, decongestive agents and vaccines. The content of the product according to the invention in said compositions is generally higher than 0.1%.

Said compositions may be administered orally, rectally, parenterally or as aerosols.

In human therapy, the doses depend on the desired effect. They may be in the range of 10 to 50 mg per day for an adult.

The following examples, given without limitation, illustrate the preparation of hydrosoluble substances according to the invention.

EXAMPLE 1

100 g of bacterial residues obtained from Mycobacterium tuberculosis var. hominis, Peurois strain, according to the method of A. Aebi and coll are ground and homogenized in 500 cm$^3$ of water by means of a grinder (Vetra-Turrax).

After stirring during 5 hours at 20°C and centrifugation for 30 minutes at 4°C (4000 r.p.m.) the supernatant layer is heated to 80°C. Ammonium sulfate is then added to obtain a 40% saturated solution. After 12 hours at 4°C and centrifugation for 30 minutes a precipitate ($P_{40}$) is obtained.

Ammonium sulfate is added to the supernatant layer to obtain a 70% saturation for 30 minutes. Under the same conditions a precipitate ($P_{70}$) is obtained. The $P_{40}$ and $P_{70}$ precipitates and the last supernatant layer obtained ($S_{70}$) are then dialyzed separately against distilled water. The various solutions which do not dialyze are freeze-dried. There is thus obtained 1.2g of fraction $P_{40}$, 1.4g of fraction $P_{70}$ and 0.9 g of fraction $S_{70}$ containing the major portion of the biologically active substance.

This latter fraction is purified by chromatography on DEAE-cellulose equilibrated with a 0.05 M pH 7 phosphate buffer, eluting with a 0.05 M pH 3 sodium citrate buffer. 400 mg purified poly-PA are thus obtained.

After filtration on Biogel P10, and eluting with water, 150 mg highly purified Poly-PA is obtained.

The composition after the Poly-PA obtained is determined as follows:

the amino-acid and amino-sugar composition is determined by means of an autoanalyzer (Technicon type) after total hydrolysis with 6N hydrochloric acid at 110°C for 18 hours and 6 hours respectively, the non-amine neutral sugar composition is determined after hydrolysis with 2N hydrochloric acid for 2 hours at 110°C, qualitatively by paper chromatography [Whatman N° 1; solvent: butanol-pyridine-water (6-4-3) by volume] and quantitatively by the means of a sugars-autoanalyzer (Technicon type).

lipid determination is effected by their layer chromatography on silica gel after total hydrolysis and ether extraction.

The purified Poly-PA previously obtained has the following characteristics:

appearance: pulverulent white powder composition a. amino acids (molecular ratio): alanine (3) glutamic acid (2), $\alpha,-\alpha'$ diaminopimelic acid (2), b. amino sugars (molecular ratio): N-acetylglucosamine (2), N-glycolylmuramic acid (2); presence of N-acetylgalactosamine, c. non amine reducing sugars: arabinose, galactose; presence of mannose d. lipids: less than 0.5% the aminoacid content is 6.2%, the amino-sugar content is 7–8% and the rest consists of non amino reducing sugars.

molecular weight (calculated on the basis of 3 alanine residues per molecule): 14,000 ± 2000 sedimentation constant: 2

EXAMPLE 2

20g of bacterial residues obtained from Mycobacterium tuberculosis var. hominis, strain $H_{37}Ra$ in 250 cm$^3$ of a pyridine-acetic anhydride mixture (3-2 by volume) is stirred for 36 hours at 28°C. Then 2500 cm$^3$ of ethyl alcohol is added and stirred for one night. The insoluble portion is separated by centrifugation (4,000 r.p.m.) The supernatant layer is concentrated to dryness under low pressure. The residue is added to 200 cm$^3$ of water. The waterinsoluble portion is separated by centrifugation (4,000 r.p.m.). The supernatant layer is filtered through a Biogel P10 column. 100 mg of hydrosoluble substance A are obtained after freeze-drying.

The composition of substance A is determined in the following manner:

the aminoacid and aminosugar composition is determined by means of an autoanalyzer (Technicon type) following total hydrolysis with 6N hydrochloric acid at 110°C for 18 hours and 6 hours respectively.

the non amino sugar composition is determined, after hydrolysis with 2N hydrochloric acid for 2 hours at 110°C, qualitatively by paper chromatography [Whatman N° 1; solvent: butanol-pyridine-water (6-4-3) by volume)] and quantitatively by gas chromatography with a sugar autoanalyzer, after methylation and silylation using a HEWLETT-PACKARD chromatograph.

lipid determination is effected by thin layer chromatography on silica gel after total hydrolysis and ether extraction.

The hydrosoluble substance A previously obtained has the following characteristics:

appearance: pulverulent yellow powder composition a. amino acids (molecular ratio): alanine (3), glutamic acid (2), $\alpha,\alpha'$-diaminopimelic acid (2), b. amino sugars (molecular ratio): N-acetylglycosamine (2), N-acetylmurmic acid (2)

c. non amino reducing sugars: mannose, glucose; presence of arabinose, absence of galactose.

d. absence of lipids the content of aminoacids is 31 ± 5%, and the content of amino-sugars is 25 ± 5%, the rest consisting of non amine reducing sugars (11%) and acetyl (11%) and acetyl functions fixed to the amino or non amino reducing sugars by acetylation
molecular weight (calculated on the basis of 3 alanine residues per molecule): 4,000 ± 200
sedimentation constant: 0,7

EXAMPLE 3

20g of bacterial residues obstained from Mycobacterium tuberculosis var. hominis, Test strain, in 250 cm³ of pyridine are stirred for 36 hours at 28°C. Then 2500 cm³ of ethyl alcohol are added and the whole is stirred again for one night. The insoluble portion, which is separated by centrifugation, is homogenized in 100 cm³ of water by means of a grinder (Ultra-Turrax).

After stirring for 48 hours at 40°C and centrifugation for 30 minutes at 4°C (4000 r.p.m.) the supernatant layer is heated to 80°C. Ammonium sulfate is then added in order to obtain a 40% saturated solution. After 12 hours at 4°C and centrifugation for 30 minutes, a precipitate ($P_{40}$) is obtained.

Ammonium sulfate is added to the supernatant layer in order to obtain a 70% saturated solution.

After 12 hours at 4°C and centrifugation for 30 minutes under the same conditions a precipitate ($P_{70}$) is obtained.

The $P_{40}$, $P_{70}$ precipitates and the last supernatant layer obtained ($S_{70}$) are then dialyzed separately against distilled water. The various solutions which do not dialyze are freeze-dried. A fraction $P_{40}$, a fraction $P_{70}$ and 0.8 g of fraction $S_{70}$ containing the major portion of the biologically active substances are thus obtained.

Said last fraction is purified by chromatography on DEAE-cellulose equilibrated with a 0.05M pH 7 phosphate buffer by eluting with an 0.05 M pH 3 sodium citrate buffer. After dialyzing and freeze-drying the corresponding fractions, 0.15g. hydrosoluble substance B and 0.1g hydrosoluble substance C are obtained.

The composition of substance C is determined according to the methods described in example 2.

The hydrosoluble substance C previously obtained has the following characteristics:
appearance: white powder after freezedrying.
composition a. amino acids (molecular ratio): alanine (3), glutamic acid (2), $\alpha$-$\alpha'$-diaminopimelic acid (2),
b. amino sugars (molecular ratio): N-acetylglycosamine (2), N-glycolylmuramic acid (2),
c. non amino reducing sugars: arabinose, galactose, mannose,
d. absence of lipids the aminoacid content is 16 ± 3%, the amino sugar content is 16 ± 3%, the rest consists of non amino reducing sugars.

molecular weight (calculated on the base of 3 alanine residues per molecule): 6,000 ± 500.

What we claim is:

1. A process for the preparation of a hydrosoluble extract of delipidated D-wax-containing mycobacteria, said extract having a molecular weight in the range of about 3,500 to 30,000, said process consisting essentially of extracting a bacterial residue of said delipidated mycobacteria with water, separating the aqueous solution from the undissolved residue, adding a salt to the aqueous solution in amount sufficient to precipitate a portion of the solute, separating the precipitate from the salt solution, separating the dissolved salt from the extract dissolved in said solution, subjecting the salt-free extract to chromatographic fractionation, and eluting and recovering a fraction which, upon freeze-drying, is a pulverulent white powder which contains (a) alanine, glutamic acid and $\alpha,\alpha'$-diaminopimelic acid in a molar ratio of about 3:2:2, (b) N-acetylglucosamine and N-glycolylmuramic acid in approximately equimolar amounts and a small amount of N-acetylgalactosamine, (c) arabinose, galctose and mannose, and (d) less than about 0.5% of lipids.

2. The process of claim 1 wherein the salt is ammonium sulfate.

3. The process of claim 1 wherein separation of the precipitates is effected by centrifugation.

4. The process of claim 1 wherein the dissolved salt is separated by dialysis.

5. The process of claim 1 wherein the salt is ammonium sulfate, the precipitates are separated by centrifugation and the dissolved salt is separated from the dissolved extract by dialysis.

6. The process of claim 5 wherein the mycobacteria are Mycobacteria tuberculosis, var-hominis.

* * * * *